(12) United States Patent
Takai et al.

(10) Patent No.: US 9,055,895 B2
(45) Date of Patent: Jun. 16, 2015

(54) OPHTHALMOLOGIC PHOTOGRAPHING APPARATUS, AND ITS PHOTOGRAPHING METHOD

(75) Inventors: Motoya Takai, Nagareyama (JP); Manabu Wada, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 658 days.

(21) Appl. No.: 12/860,262

(22) Filed: Aug. 20, 2010

(65) Prior Publication Data

US 2011/0051086 A1 Mar. 3, 2011

(30) Foreign Application Priority Data

Aug. 28, 2009 (JP) ................................. 2009-198413
Jul. 9, 2010 (JP) ................................. 2010-156918

(51) Int. Cl.
*A61B 3/12* (2006.01)
*A61B 5/00* (2006.01)
*A61B 3/107* (2006.01)

(52) U.S. Cl.
CPC .................. *A61B 3/12* (2013.01); *A61B 5/0059* (2013.01); *A61B 3/107* (2013.01)

(58) Field of Classification Search
CPC ........ A61B 3/103; A61B 3/1015; A61B 3/14; A61B 3/12
USPC .......................................... 351/205–206, 246
See application file for complete search history.

(56) References Cited

U.S. PATENT DOCUMENTS

| | | | |
|---|---|---|---|
| 5,181,055 A | 1/1993 | Sano et al. | |
| 5,287,129 A * | 2/1994 | Sano et al. | 351/233 |
| 5,291,231 A * | 3/1994 | Hideshima et al. | 351/208 |
| 6,611,704 B1 * | 8/2003 | van Best et al. | 600/476 |
| 2002/0147383 A1 * | 10/2002 | Weber et al. | 600/109 |
| 2006/0077344 A1 | 4/2006 | Kashiwagi et al. | |
| 2006/0244913 A1 * | 11/2006 | Gellermann et al. | 351/205 |
| 2007/0132951 A1 * | 6/2007 | Suzuki | 351/206 |
| 2008/0273172 A1 * | 11/2008 | Spaide | 351/206 |

FOREIGN PATENT DOCUMENTS

| | | |
|---|---|---|
| JP | S63-105739 A | 5/1988 |
| JP | H04-092639 A | 3/1992 |
| JP | H04-352934 A | 12/1992 |
| JP | H07-327930 A | 12/1995 |
| JP | 2002-200047 A | 7/2002 |
| JP | 2003-070747 A | 3/2003 |
| JP | 2006-122647 A | 5/2006 |
| JP | 2009-066109 A | 4/2009 |

* cited by examiner

*Primary Examiner* — James Greece
(74) *Attorney, Agent, or Firm* — Canon USA Inc IP Division

(57) ABSTRACT

An ophthalmologic photographing apparatus includes a light source configured to emit photographing light for illuminating a subject's eye through an illumination optical system, a changing unit configured to change a light emission amount of the light source, a selecting unit configured to select at least one of a plurality of photographing modes for photographing the subject's eye, a storage unit configured to store the changed light emission amount by the changing unit as a changed value during the photography in the photographing mode selected by the selecting unit, and a setting unit configured to set a light emission amount at a start of the photography to a light emission amount which is set beforehand as an initial state of the light source or to the changed value according to the plurality of photographing modes.

19 Claims, 7 Drawing Sheets

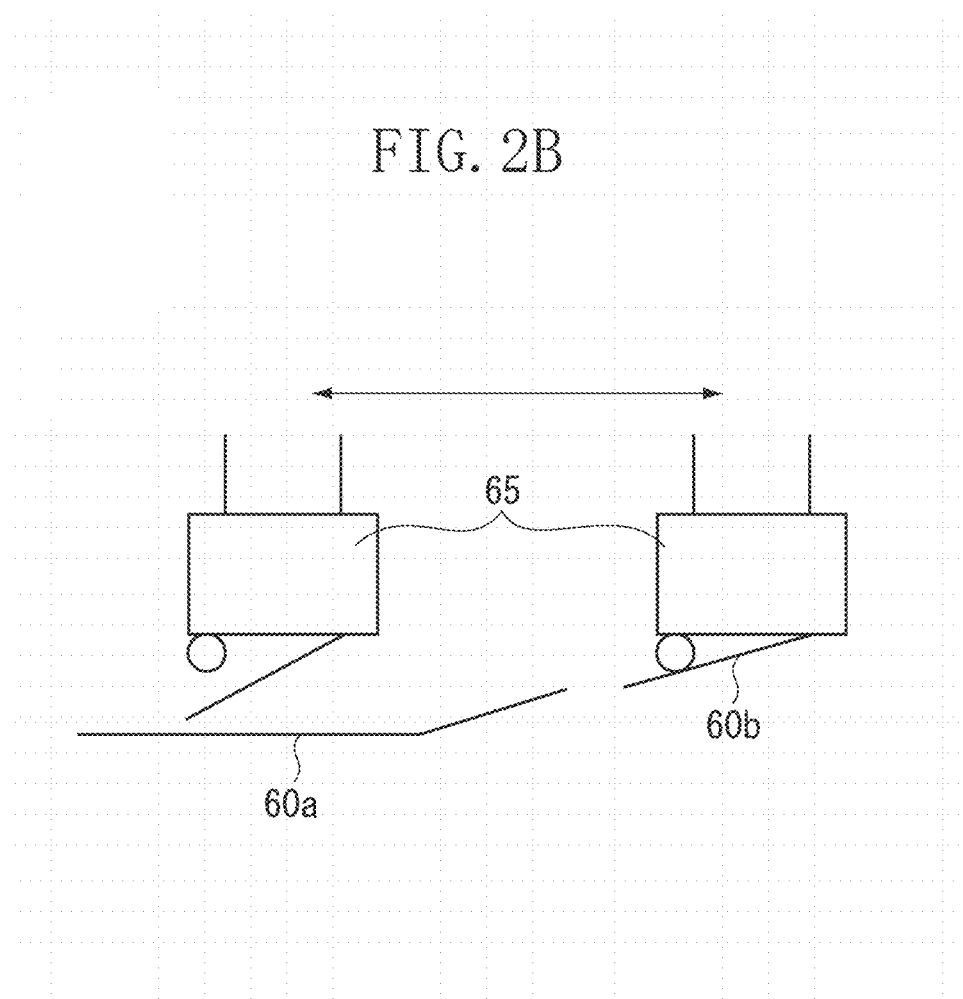

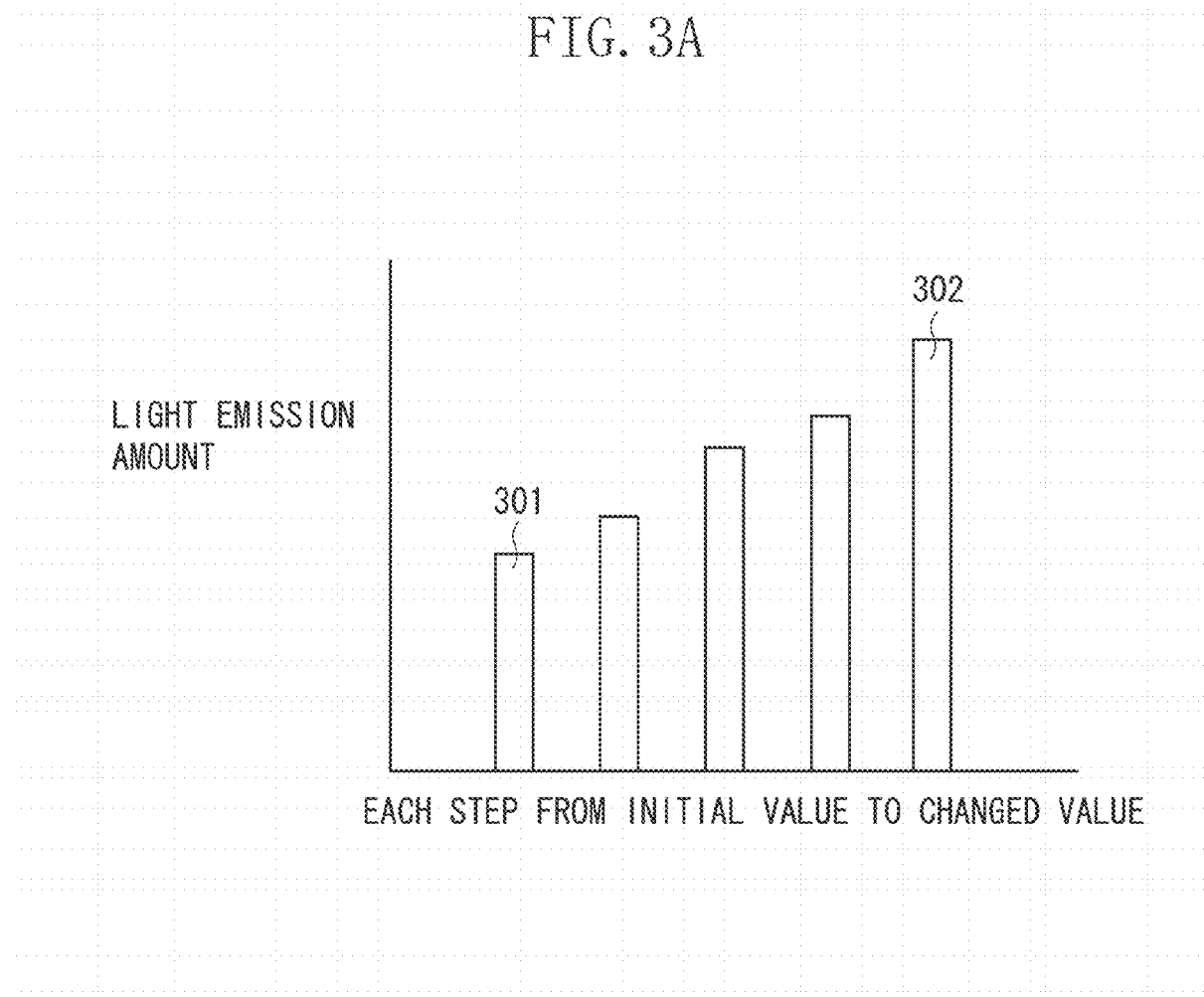

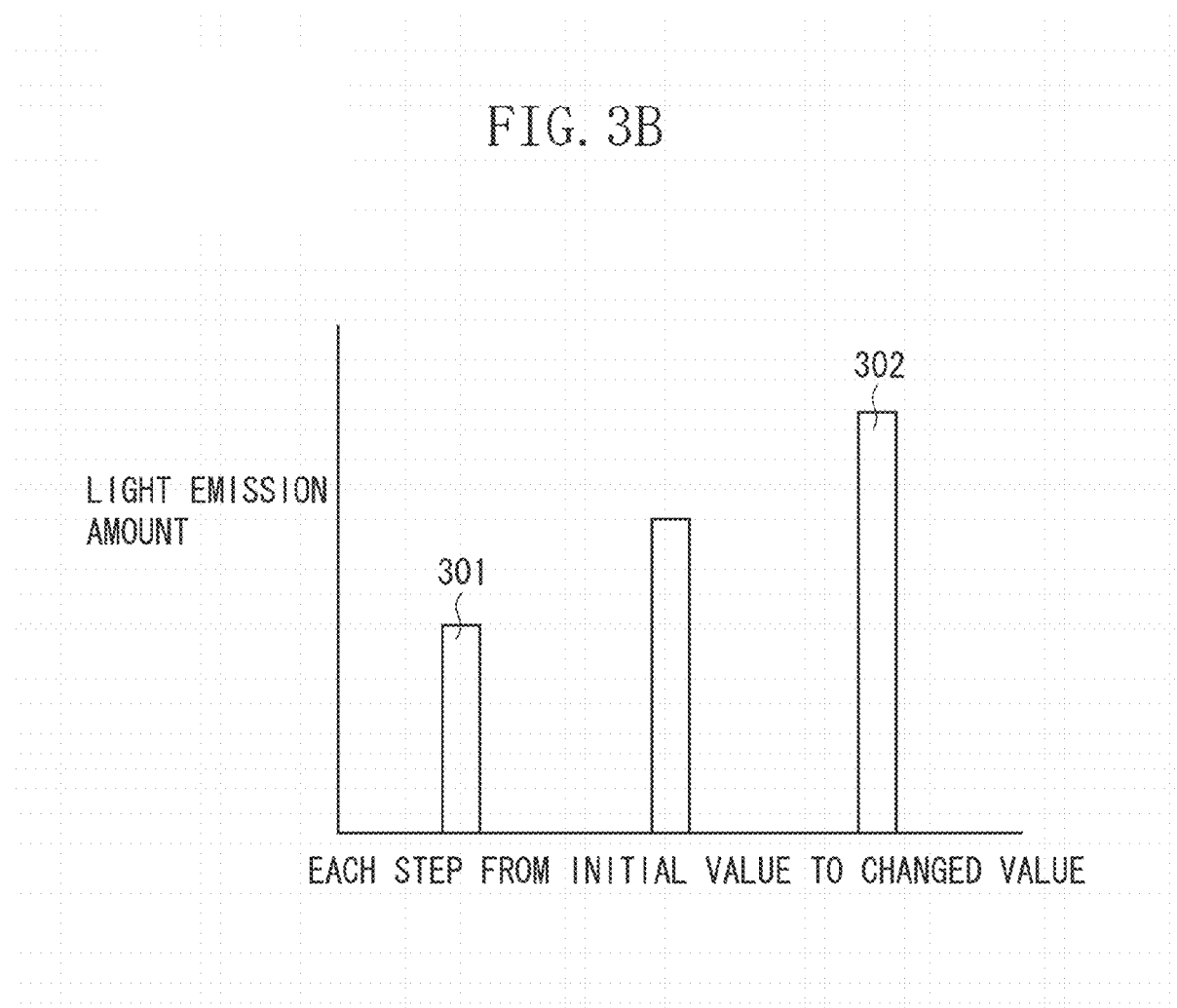

OPHTHALMOLOGIC PHOTOGRAPHING APPARATUS, AND ITS PHOTOGRAPHING METHOD

BACKGROUND OF THE INVENTION

1. Field of the Invention

The present invention relates to an ophthalmologic photographing apparatus that is used in an ophthalmic hospital, and its photographing method.

2. Description of the Related Art

A fundus camera that photographs a fundus of a subject's eye has widely been known as an ophthalmologic photographing apparatus. The fundus camera can photograph a fundus using a plurality of photographing methods ("photographing method" is sometimes referred to as "photographing mode" hereinafter) which include infrared fluorescent photography and visible fluorescent photography. In this case, a user sometimes changes a light emission amount of a light source during the photography. Japanese Patent Application Laid-Open No. 2002-200047 discusses a technique in which the light emission amounts for the plurality of photographing methods are recorded, and the photographing is started with the recorded light emission amount in the next photographing.

In the case of fundus autofluorescence photography (the photography in which lipofuscin that is a waste product on retinal pigment epithelium is excited without using a fluorescent agent), it has been found by the applicant of the present invention that individual differences of the excited light in age, race, or sex are small. The applicant of the present invention has also found that, when a subject's eye having a lesion such as a cataract is photographed with fundus autofluorescence, the light emission amount of the light source has to be lowered. A light-transmitting part is opacified in the cataract. Therefore, when the subject's eye having the cataract is photographed with an ordinary light emission amount, a light scatter at the opacified part might affect imaging of the lesion.

It is considered the case in which a subject changes the light emission amount in Japanese Patent Application Laid-Open No. 2002-200047. In this application, the light emission amount that is changed for photographing a subject before the change is also applied to a subject after the change, even if the subject after the change is photographed. In this case, when the subject's eye has a cataract or other lesion, the light emission amount (initial value) at the start of the photography has to be reset to a fixed value (a light emission amount that is set beforehand as an initial state of the light source), so that an operation load to a user may increase.

SUMMARY OF THE INVENTION

According to an aspect of the present invention, an ophthalmologic photographing apparatus includes a light source configured to emit photographing light for illuminating a subject's eye through an illumination optical system, a changing unit configured to change a light emission amount of the light source, a selecting unit configured to select at least one of a plurality of photographing modes for photographing the subject's eye, a storage unit configured to store the changed light emission amount by the changing unit as a changed value during the photography in the photographing mode selected by the selecting unit, and a setting unit configured to set a light emission amount at a start of the photography to a light emission amount which is set beforehand as an initial state of the light source or to the changed value according to the plurality of photographing modes.

According to another aspect of the present invention, a method for performing ophthalmologic photographing includes generating photographing light for illuminating a subject's eye through an illumination optical system, selecting a first photographing mode that photographs the subject's eye, storing a changed light emission amount as a changed value during the photography in the first photographing mode, setting the light emission amount at a start of the photography in the first photographing mode to the changed value, selecting a second photographing mode that photographs the subject's eye, and setting the light emission amount at a start of the photography in the second photographing mode to a light emission amount that is set beforehand as an initial state of the light source.

According to yet another aspect of the present invention, an ophthalmologic photographing apparatus includes a light source configured to emit photographing light for illuminating a subject's eye through an illumination optical system, a changing unit configured to change a light emission amount of the light source, a selecting unit configured to select a first photographing mode for photographing the subject's eye and a second photographing mode that is different from the first photographing mode, a storage unit configured to store the changed light emission amount by the changing unit as a changed value during the photography in the first photographing mode, and a setting unit configured to set the light emission amount at the start of the photography to the changed value when the first photographing mode is selected, and to set the light emission amount at the start of the photography to a light emission amount which is set beforehand as an initial state of the light source when the second photographing mode is selected.

According to the ophthalmologic photographing apparatus of the present invention, when a photographing mode such as fundus autofluorescence photography is selected, a changed light emission amount can be stored as a changed value (stored value) every photographing operation. Therefore, the light emission amount (initial value) at the start of the photography can be set to the changed value or the fixed value (the light emission amount that is set beforehand as the initial state of the light source) according to the photographing mode. Thus, resetting the light emission amount is unnecessary, and a photographing efficiency can be improved.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIGS. 2A and 2B illustrate the fundus camera.

FIGS. 3A and 3B illustrate a setting of light quantity.

DESCRIPTION OF THE EMBODIMENTS

Various exemplary embodiments, features, and aspects of the invention will be described in detail below with reference to the drawings.

An ophthalmologic photographing apparatus according to a first exemplary embodiment will be described with reference to FIGS. 1 to 4. A fundus camera will be described in the present exemplary embodiment. However, the ophthalmologic photographing apparatus according to the present invention is not limited to the fundus camera. For example, the present invention is applicable to an apparatus that photographs an anterior eye such as a cornea.

Figure 1:
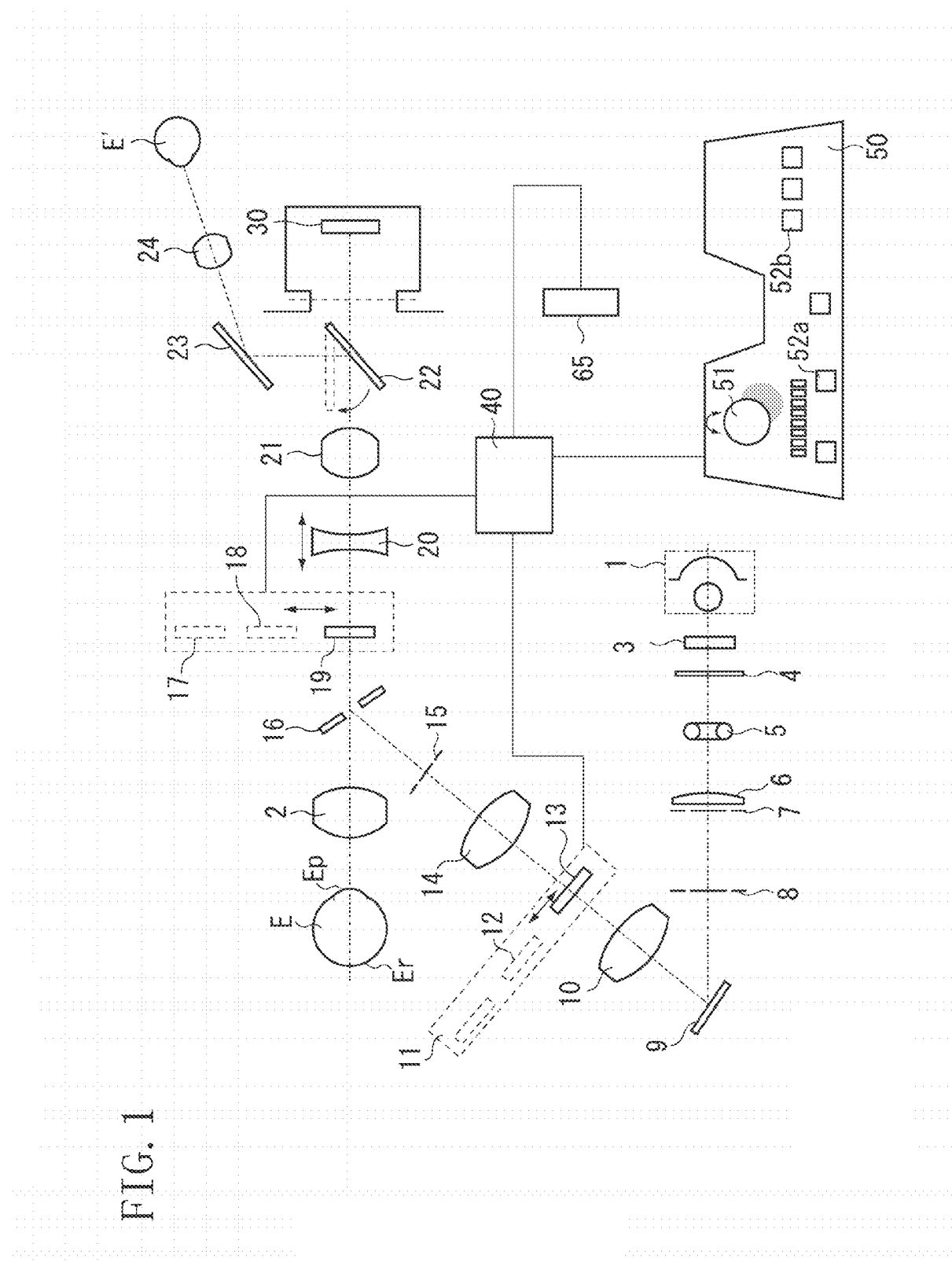
FIG. 1 illustrates a configuration of a fundus camera.

FIG. 1 illustrates a configuration of a fundus camera that includes an observation light source which produces visible light or infrared light and can emit such light to a subject's eye as illumination light. On an optical path from the observation light source 1 to an objective lens 2, two mirrors, which are a perforated mirror 16 and a folding mirror 9, are arranged. A visible cut filter 3 which does not pass visible wavelength, a diffusion plate 4, and a photographing light source 5 such as a flash lamp are sequentially arranged between the observation light source 1 to the folding mirror 9. Further, a condenser lens 6 for enhancing efficiency of using the light emitted from the flash lamp, and a pupil stop 7 which is disposed on a position substantially conjugate with a pupil position of the subject's eye and has an annular opening are also arranged. A crystalline lens stop 8 that has an annular opening for separating an illumination light flux and a photographing light flux from each other is also arranged to prevent entrance of harmful light (reflection light) from the crystalline lens of the subject's eye due to the illumination light flux.

Relay lenses 10 and 14 are arranged at the rear of the folding mirror 9, and between the relay lenses 10 and 14, an ultraviolet (UV) cut filter 11, a visible fluorescence exciter filter 12, and an autofluorescence exciter filter 13 are arranged which can be exchanged on the optical axis. A cornea stop 15 that has an annular opening for separating the illumination light flux and the photographing light flux from each other is also arranged to prevent entrance of the harmful light (reflection light) from the cornea of the subject's eye due to the illumination light flux. Thus, a fundus illumination optical system that illuminates from a fundus Er to a pupil Ep of a subject's eye E is configured.

A drive system (not illustrated) of the UV cut filter 11, the visible fluorescence exciter filter 12, and autofluorescence exciter filter 13 is connected to a control unit 40 which is formed with using a central processing unit (CPU).

A dummy glass 17, a visible fluorescence barrier filter 18, and autofluorescence barrier filter 19 are arranged on an optical path in a transmitting direction of the perforated mirror 16 and can be exchanged on the optical axis. A focusing lens 20, a photographic lens 21, and a flip-up mirror 22 which can be raised up are sequentially arranged.

The reflection light reflected from the fundus Er passes through the mirror 23 and the lens 24 to be directed to an eye E' of an examiner, and observed during the observation with visible light. The examiner may be a doctor or a laboratory technician who conducts an examination. An image sensor 30 that can be attached or detached is arranged at the rear of the flip-up mirror 22.

A drive system (not illustrated) of the dummy glass 17, the visible fluorescence barrier filter 18, and the autofluorescence barrier filter 19 is connected to the control unit 40, like the case in the illumination optical system. Thus, a fundus imaging/observation optical system that images the fundus Er of the subject's eye E is configured.

The UV cut filter 11, the visible fluorescence exciter filter 12, and the autofluorescence exciter filter 13 are inserted into or retreated from the optical path of the illumination optical system according to the photographing method. The insertion and retreat of these components and the insertion and retreat of the dummy glass 17, the visible fluorescence barrier filter 18, and the autofluorescence barrier filter 19 into the optical path of the imaging/observation optical system are combined, so that the fundus camera serving as the ophthalmologic photographing apparatus can perform photographing according to the plurality of photographing methods.

An operation unit for the examiner will next be described.

The fundus camera is provided with an operation panel 50 serving as an operation unit for the examiner. The operation panel 50 is connected to the control unit 40. The operation panel 50 includes a volume 51 for setting a light emission amount of the observation light during observation of the fundus, a control switch 52a for determining a light emission amount (light emission amount of the photographing light) of the flash lamp during when the fundus is photographed, and a photographing-method switch 52b that determines various photographing states such as the fluorescent photography or color photography. The various switches 52a, 52b, . . . are prepared in number for setting the respective photographing methods. As described above, the operation panel 50 is provided with the switches 52 which serve as a selecting unit and correspond to the plurality of photographing methods (sometimes referred to as the plurality of photographing modes). The selecting unit may be the one capable of selecting the photographing method. For example, the selecting unit may be configured as a dial, a moving bar, or the like.

Figure 2A:
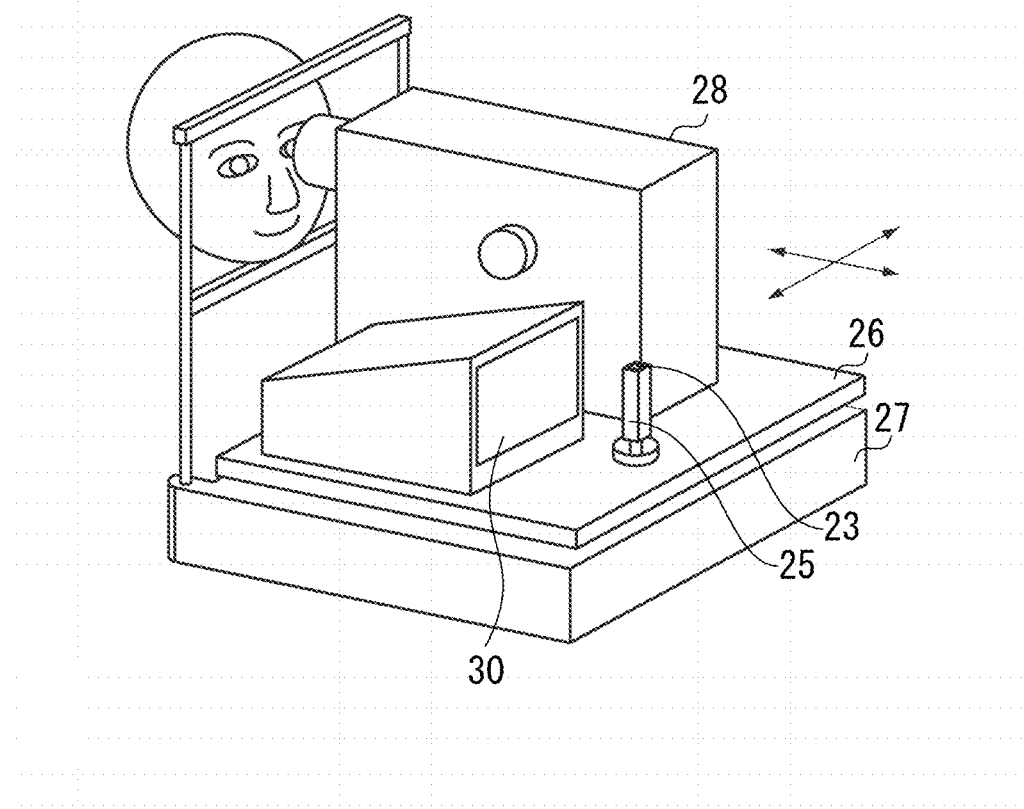

FIGS. 2A and 2B illustrate an outer appearance of the fundus camera. A main body 28 that incorporates the above described optical system therein is placed onto a rack 26 that can freely move in a horizontal direction (directions indicated by arrows in the figure) to a base 27. The rack 26 is provided with an operation stick 25 including a photographing switch 23 and a rack position detecting unit 65 which constitutes a left/right eye detecting unit for detecting the left/right eye. The rack position detecting unit 65 is connected to the control unit 40. The examiner uses the operation stick 25 to adjust the position of the main body with respect to the subject as illustrated in FIG. 2A.

FIG. 2B illustrates the rack position detecting unit 65 (e.g., a microswitch) that detects a lateral movement of the main body. As illustrated in FIG. 2B, a height difference is formed on a top surface of a base 60. More specifically, the base 60 has a low portion 60a and a high portion 60b. When the rack position detecting unit 65 provided at a bottom surface of a rack 61 is located above the low portion 60a of the base, the rack position detecting unit 65 is turned OFF. On the other hand, when the rack position detecting unit 65 is located above the high portion 60b of the base, the rack position detecting unit 65 is turned ON. The low portion of the base 60 is provided at a right side of the subject, while the high portion is provided at a left side of the subject. Therefore, the left/right eye detecting unit can detect which one of the left eye and the right eye of the subject is photographed by detecting ON/OFF of the rack position detecting unit 65.

Figure 4:
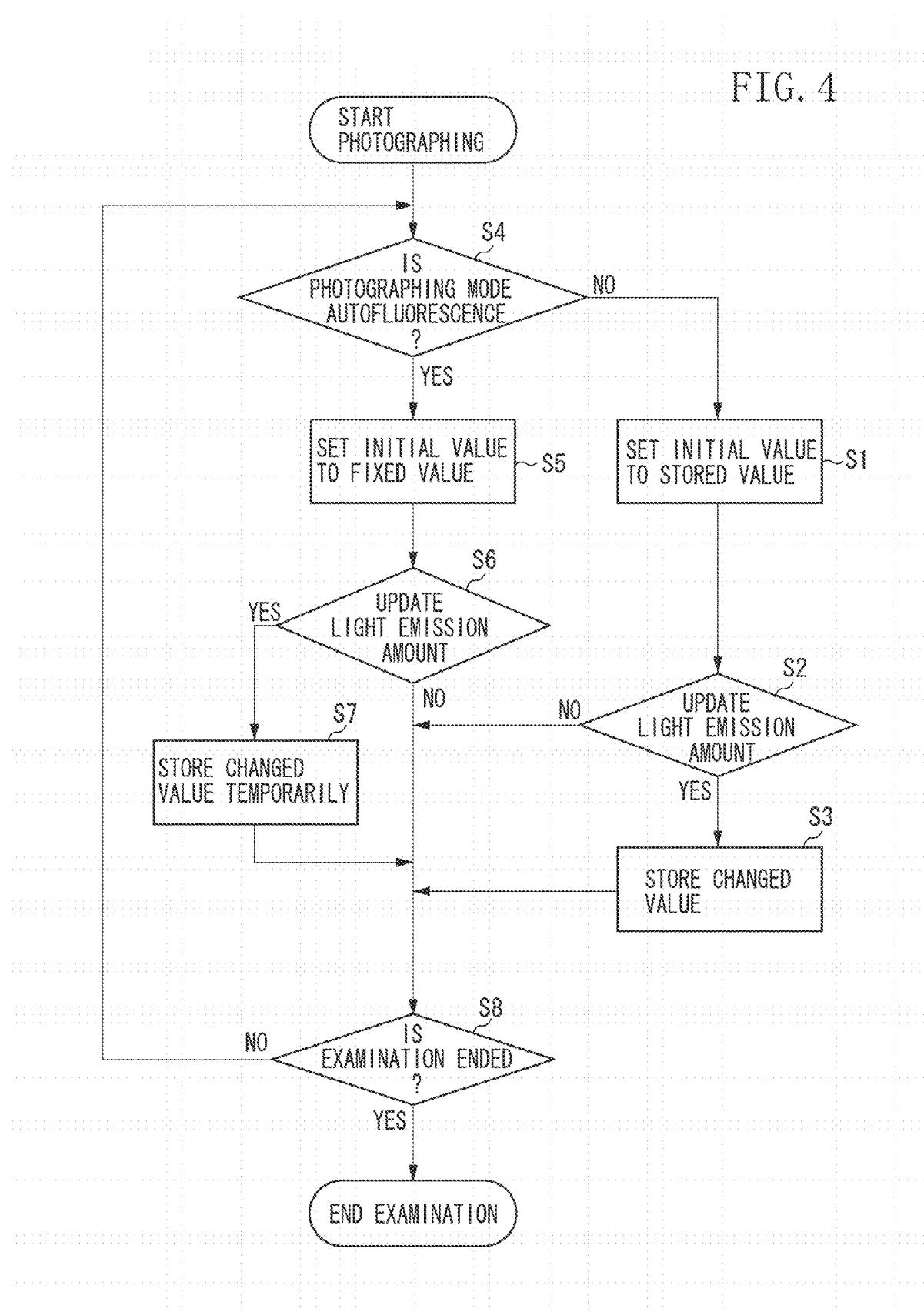
FIG. 4 is a flowchart illustrating photographing of a subject's eye according to a first exemplary embodiment.

The photography of the subject's eye according to the present exemplary embodiment will next be described with reference to a flowchart in FIG. 4.

(Visible Fluorescent Photography: a First Photographing Mode)

The examiner selects a first photographing method (sometimes referred to as a first photographing mode) by the photographing-method switch 52b which is a selecting unit in the operation panel 50. In this case, the control unit 40 performs control to insert the visible fluorescence exciter filter 12 into the optical path of the illumination optical system. Further, the control unit 40 performs control to insert the visible fluorescence barrier filter 18 into the optical path of the photographing optical system. In step S1, the setting unit for setting a light emission amount (an initial value) of the photographing light source 5 at a start of the photography sets the light emission amount at the start of the photography to a stored value stored in a storage unit (sometimes referred to as a storage section storing a light emission amount of photographing light).

The stored value can be referred to a changed light emission amount (a changed value) during the photography according to the first photographing mode. The storage unit may be provided in the control unit 40 or at an outside of the control unit 40.

In step S2, the case in which the examiner operates the control switch 52a provided in the operation panel 50 for controlling a power source of the photographing light source 5 is considered. In this case, the control switch 52a functions as a changing unit for changing the light emission amount of the photographing light source 5. In step S3, the storage unit updates the stored value from the light emission amount before the change to the changed light emission amount (changed value). The light emission amount may be indicated by a value of a voltage or a value of a current supplied to the photographing light source 5. In step S8, the light emission amount of the photographing light source 5 is unchanged until the light emission amount is updated.

(Fundus Autofluorescence Photography: a Second Photographing Mode)

In step S4, the examiner selects a second photographing method (sometimes referred to as a second photographing mode) by the photographing-method switch 52b which is the selecting unit in the operation panel 50. In this case, the control unit 40 performs control to insert the autofluorescence exciter filter 13 into the optical path of the illumination optical system. The control unit 40 also performs control to insert the autofluorescence barrier filter 19 into the optical path of the photographing optical system. In step S5, the setting unit for setting the light emission amount (an initial value) of the photographing light source 5 at the start of the photography sets the light emission amount at the start of the photography to a fixed value (the light emission amount set beforehand as the initial state of the light source). The fixed value is a fixed light emission amount set beforehand to the photographing light source 5, and it is desirably stored in the storage unit.

In step S6, when the examiner operates the control switch 52a in the operation panel 50 (YES in step S6), then in step S7, the light emission amount acts only in a decreasing (reducing) direction, and is temporarily stored in the storage unit. This process can prevent a user from erroneously setting the changed amount of the light emission amount. Thereafter, in step S8, the emission of the photographing light source 5 is maintained at the changed light emission amount until the photographing method is changed.

Figure 5:
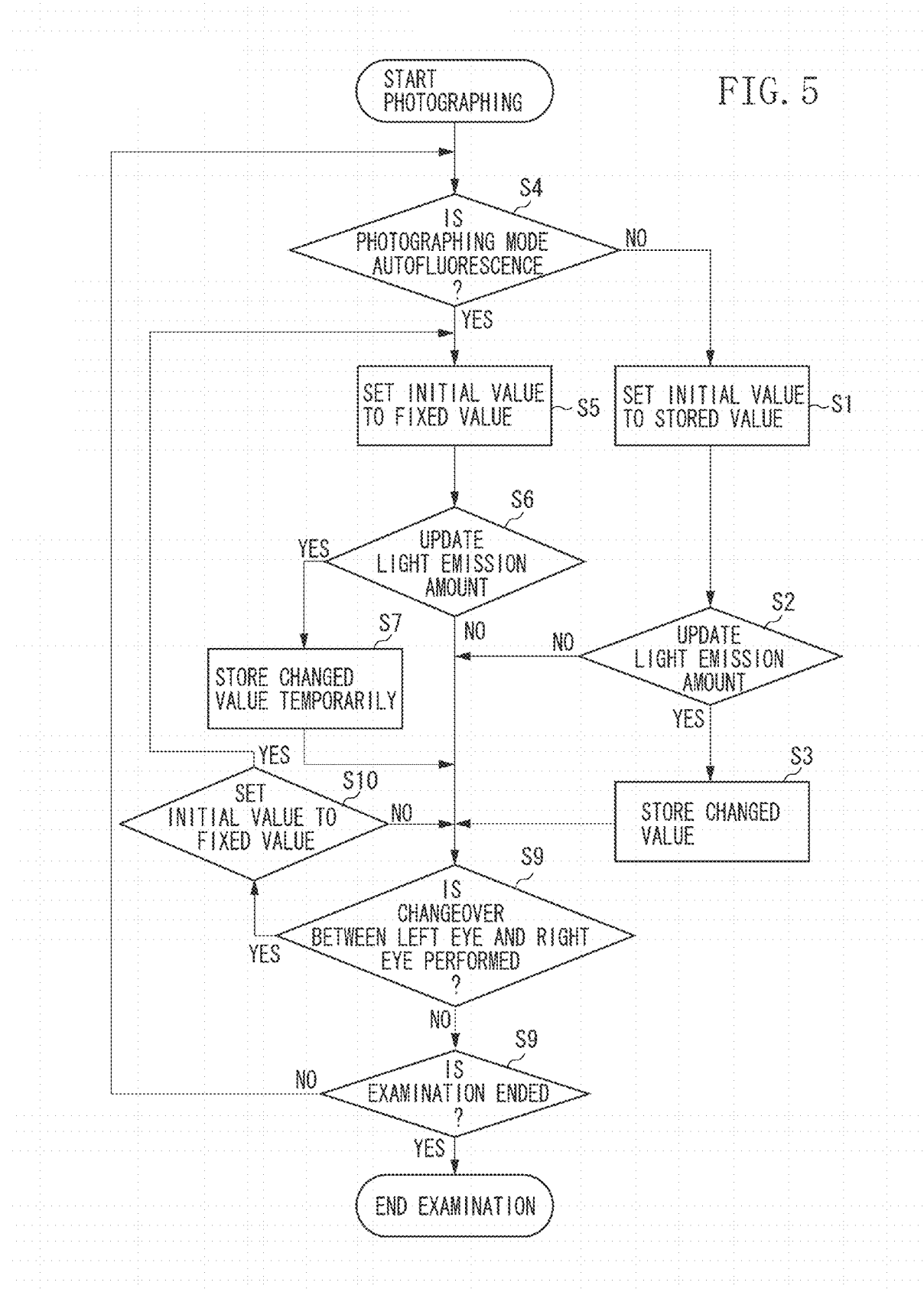
FIG. 5 is a flowchart illustrating photographing of a subject's eye according to a second exemplary embodiment.

A photographing of a subject's eye according to a second exemplary embodiment will be described with reference to a flowchart in FIG. 5. The processes similar to those in the first exemplary embodiment are identified by the same step numbers. The processes in step S1 to step S7 are similar to those in the first exemplary embodiment.

In step S9, the case in which a changeover between a left eye and a right eye of a subject is detected by a left/right eye detecting unit is considered in the present exemplary embodiment. In this case, a determining unit determines whether the light emission amount (initial value) at the start of the photography is set to the fixed value or to the changed light emission amount (changed value) by the changing unit. The determining unit may be provided in the control unit 40 or at the outside of the control unit 40. More specifically, the determining unit determines based upon a magnitude of the changed amount of the light emission amount by the changing unit with respect to a predetermined value. In step S10, when the changed amount is smaller than the predetermined value, the initial value is set to the fixed value. On the other hand, when the changed value is greater than the predetermined value, the initial value is set to the changed light emission amount.

This is because, if the subject's eye has a cataract and this symptom is serious, the similar symptom might be developed on not only one eye but also the other eye. More specifically, when the changed amount of one eye is greater than the predetermined value, it is desirable that the changed light emission amount (changed value) is applied to the other eye. In this case, it is desirable that the changed light emission amount is stored in the storage unit, and the setting unit sets the stored value.

When the symptom of one eye is minor, the similar symptom is highly possibly not developed on the other eye. More specifically, when the changed amount for one eye is smaller than the predetermined value, it is highly possible that a state of the left eye and a state of the right eye are greatly different from each other. Therefore, it is not preferable that the changed light emission amount for one eye is applied to the other eye without being changed, but it is preferable that the initial value is set to the fixed value. Thus, the initial value for the other eye can be set to the fixed value or the changed value according to the changed amount for one eye.

Accordingly, resetting is unnecessary upon the changeover between the left eye and the right eye, so that a photographing efficiency can be improved. When the subject's eye has a lesion such as a cataract, the changed amount of the light emission amount of the light source in the fundus autofluorescence photography has to be increased more than the changed amount in the conventional fluorescent photography.

Next, a degree (number of steps from the initial value to the changed value) of the change in the light emission amount by the changing unit will be described with reference to FIGS. 3A and 3B. In FIGS. 3A and 3B, an abscissa axis represents a number of operations of the control switch 52a which is the changing unit in the operation panel 50, while an ordinate axis represents the light emission amount at that point. FIG. 3A illustrates the case of the color or visible fluorescent photography, and FIG. 3B illustrates the case of the fundus autofluorescence photography.

The case in which the light emission amount is changed from an initial value 301 to a changed value 302 is considered here. In FIG. 3A, a fine adjustment in the light emission amount is required, so that it is desirable that the light emission amount is changed with five steps. On the other hand, in FIG. 3B, a fine adjustment in the light emission amount is not needed in the color or visible fluorescent photography, so that the light emission amount is changed with three steps. Accordingly, in the fundus autofluorescence photography, the light emission amount can be adjusted to the predetermined changed value with the step number smaller than that in the other photographing mode.

Aspects of the present invention can also be realized by a computer of a system or apparatus (or devices such as a CPU or MPU) that reads out and executes a program recorded on a memory device to perform the functions of the above-described embodiment (s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-198413 filed Aug. 28, 2009, and No. 2010-156918 filed Jul. 9, 2010, which are hereby incorporated by reference herein in their entirety.

What is claimed is:

1. An ophthalmologic photographing apparatus comprising:
   a selecting unit configured to select one of a plurality of photographing modes for photographing a subject's eye, wherein the plurality of photographing modes includes an autofluorescence photographing mode for autofluorescence-photographing the subject's eye illuminated with photographing light emitted from a light source;
   a determining unit configured to determine an initial value of a light emission amount of the light source to a light emission amount corresponding to the autofluorescence photography mode in a case where the autofluorescence photographing mode is selected; and
   a changing unit configured to change, in a case where the autofluorescence photographing mode is selected, the light emission amount of the light source from the determined initial value by a changed amount greater than a changed amount in a photographing mode different from the autofluorescence photographing mode.

2. The ophthalmologic photographing apparatus according to claim 1,
   wherein the determining unit determines a changed value changed by the changing unit when a first subject's eye is photographed as the initial value of the light emission amount of the light source when a second subject's eye is photographed in a case where a photographing mode different from the autofluorescence photographing mode is selected.

3. The ophthalmologic photographing apparatus according to claim 1 further comprising:
   a control unit configured to control the changing unit so as to change the light emission amount of the light source from the determined initial value to a value smaller than the initial value.

4. The ophthalmologic photographing apparatus according to claim 1, further comprising
   a left/right eye detecting unit,
   wherein, in a case where the subject's eye is changed from one eye to the other eye during the photography in the second photographing mode,
   when the changed amount of the light emission amount by the changing unit is smaller than a predetermined value, the light emission amount at the start of the photography is set to the light emission amount that is set beforehand as the initial state of the light source, and when the changed amount is greater than the predetermined value, the light emission amount at the start of the photography is set to the changed value.

5. The ophthalmologic photographing apparatus according to claim 1, wherein a visible fluorescence exciter filter is inserted into an optical path of the illumination optical system in a visible fluorescence photographing mode, and an autofluorescence exciter filter is inserted into the optical path of the illumination optical system in the autofluorescence photographing mode.

6. The ophthalmologic photographing apparatus according to claim 1, further comprising
   wherein a visible fluorescence barrier filter is inserted into an optical axis of the illumination optical system in a visible fluorescence photographing mode, and an autofluorescence barrier filter is inserted into the optical axis of the illumination optical system in the autofluorescence photographing mode.

7. The ophthalmologic photographing apparatus according to claim 1,
   wherein a photographing unit is used for photographing fundus of the subject's eye illuminated with the photographing light emitted from the light source in the light emission amount changed by the changing unit.

8. The ophthalmologic photographing apparatus according to claim 7, further comprising:
   a control unit configured to control the changing unit so as to change the light emission amount of the light source from the determined initial value to a value smaller than the initial value.

9. The ophthalmologic photographing apparatus according to claim 7, further comprising:
   a control unit configured to control the changing unit so as to be prohibited from changing the light emission amount of the light source from the determined initial value to a value larger than the initial value.

10. An ophthalmologic photographing apparatus comprising:
    a selecting unit configured to select one of a plurality of photographing modes for photographing a subject's eye illuminated with photographing light emitted from a light source;
    a changing unit configured to change a light emission amount of the light source from an initial value; and
    a determining unit configured to determine, in a case where the subject's eye to be photographed in a selected photographing mode is changed from one of left and right eyes to an other of the left and right eyes and a change amount from the initial value of the light emission amount of the light source in photographing the one of the left and right eyes is greater than a threshold value, the initial value of the light emission amount of the light source in photographing the other of the left and right eyes to be a change value changed by the change amount.

11. A method for performing ophthalmologic photographing, the method comprising:
    selecting one photographing mode from a plurality of photographing modes including an autofluorescence photographing mode for autofluorescence-photographing a subject's eye illuminated with photographing light emitted from a light source;
    determining an initial value of a light emission amount of a light source to be a light emission amount corresponding to the autofluorescence photographing mode in a case where the autofluorescence photographing mode is selected; and
    changing, in a case where the autofluorescence photographing mode is selected, the light emission amount of the light source from the determined initial value by a changed amount greater than a changed amount in a photographing mode different from the autofluorescence photographing mode.

12. The method according to claim 11,
wherein the changed value during the photography with the fundus autofluorescence photography is smaller than the light emission amount that is set beforehand as the initial state of the light source.

13. A program that executes the method according to claim 11 with a computer.

14. An ophthalmologic photographing apparatus comprising:
a selecting unit configured to select one photographing mode from a plurality of photographing modes including an autofluorescence photographing mode for autofluorescence-photographing a subject's eye illuminated with photographing light emitted from a light source; and
a changing unit configured to change, in a case where the autofluorescence photographing mode is selected, a light emission amount of the light source by a changed amount greater than a changed amount in a photographing mode different from the autofluorescence photographing mode.

15. The ophthalmologic photographing method according to claim 14, further comprising:
a determining unit configured to determine an initial value of the light emission amount of the light source to a light emission amount corresponding to the autofluorescence photographing mode in a case where the autofluorescence photographing mode is selected by the selecting unit,
wherein the changing unit is configured to change the light emission amount of the light source from the determined initial value by the changed amount greater than the changed amount in the photographing mode different from the autofluorescence photographing mode, in a case where the autofluorescence photographing mode is selected by the selecting unit, and
wherein a photographing unit is used for photographing fundus of the subject's eye illuminated with photographing light emitted from the light source in the light emission amount changed by the changing unit.

16. An ophthalmologic photographing method comprising:
selecting one photographing mode from a plurality of photographing modes including an autofluorescence photographing mode for autofluorescence-photographing a subject's eye illuminated with photographing light emitted from a light source; and
changing, in a case where the autofluorescence photographing mode is selected, a light emission amount of the light source by a changed amount greater than a changed amount in a photographing mode different from the autofluorescence photographing mode.

17. An ophthalmologic photographing method comprising:
selecting one of a plurality of photographing modes for photographing a subject's eye illuminated with photographing light emitted from a light source;
changing a light emission amount of the light source from an initial value; and
determining, in a case where the subject's eye to be photographed in a selected photographing mode is changed from one of left and right eyes to an other of the left and right eyes and a change amount from the initial value of the light emission amount of the light source in photographing the one of the left and right eyes is greater than a threshold value, the initial value of the light emission amount of the light source in photographing the other of the left and right eyes to be a change value changed by the change amount.

18. A program that executes the method according to claim 16 with a computer.

19. A program that executes the method according to claim 17 with a computer.

* * * * *